(12) United States Patent
Watanabe et al.

(10) Patent No.: US 8,911,685 B2
(45) Date of Patent: Dec. 16, 2014

(54) AUTOMATED ANALYZER

(75) Inventors: Atsushi Watanabe, Hitachinaka (JP); Shigeki Matsubara, Hitachinaka (JP); Teruhiro Yamano, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 201 days.

(21) Appl. No.: 13/147,633

(22) PCT Filed: Feb. 3, 2010

(86) PCT No.: PCT/JP2010/000622
§ 371 (c)(1),
(2), (4) Date: Sep. 9, 2011

(87) PCT Pub. No.: WO2010/095375
PCT Pub. Date: Aug. 26, 2010

(65) Prior Publication Data
US 2012/0114526 A1    May 10, 2012

(30) Foreign Application Priority Data
Feb. 20, 2009    (JP) .................... 2009-037325

(51) Int. Cl.
| G01N 35/00 | (2006.01) |
| G01N 35/02 | (2006.01) |
| G01N 35/10 | (2006.01) |
| G01F 23/00 | (2006.01) |
| G01F 23/26 | (2006.01) |
| G01N 35/04 | (2006.01) |

(52) U.S. Cl.
CPC .......... *G01N 35/025* (2013.01); *G01N 35/1002* (2013.01); *G01F 23/00* (2013.01); *G01N 35/1009* (2013.01); *G01N 2035/00673* (2013.01); *G01N 2035/0443* (2013.01); *G01N 2035/1025* (2013.01); *G01F 23/263* (2013.01)
USPC ............ 422/517; 422/501; 422/509; 422/519

(58) Field of Classification Search
CPC ............................................. G01N 2035/1025
See application file for complete search history.

(56) References Cited

U.S. PATENT DOCUMENTS

| 4,818,492 A | 4/1989 | Shimizu |
| 4,970,468 A | 11/1990 | Ishizawa et al. |
| 2005/0123445 A1* | 6/2005 | Blecka et al. .................. 422/64 |
| 2008/0286158 A1 | 11/2008 | Watanabe et al. |
| 2011/0104810 A1* | 5/2011 | Shiba et al. .................... 436/50 |

FOREIGN PATENT DOCUMENTS

| JP | 62-218818 A | 9/1987 |
| JP | 63-259420 A | 10/1988 |
| JP | 2-59619 A | 2/1990 |
| JP | 11-241973 A | 9/1999 |
| JP | 2000-275251 A | 10/2000 |

(Continued)

*Primary Examiner* — P. Kathryn Wright
(74) *Attorney, Agent, or Firm* — Mattingly & Malur, PC

(57) ABSTRACT

Disclosed is an automated analyzer intended for qualitative/quantitative analysis of blood, urine, and other biological samples, and including a reagent disk for mounting a plurality of reagent containers thereon, wherein any errors in liquid-level measurement due to oscillation of a reagent liquid surface during rotation of the reagent disk are minimized, even when reagent containers of a large capacity are mounted. If a predetermined constant cycle time is defined as one unit, the reagent disk with reagent containers mounted thereon is transported to a liquid-level detection position using at least two units when a liquid level of a reagent is measured.

5 Claims, 13 Drawing Sheets

(56) References Cited

FOREIGN PATENT DOCUMENTS

| JP | 2002-48801 | A | 2/2002 |
| JP | 2002-048801 | A | 2/2002 |
| JP | 2002-162403 | A | 6/2002 |
| JP | 2004-271266 | A | 9/2004 |
| JP | 3845305 | B2 | 8/2006 |
| JP | 2008-309777 | A | 12/2008 |

* cited by examiner (a) LIQUID-SURFACE HEIGHT IN 1-STEP SCHEME OF REAGENT DISK ROTATION (b) LIQUID-SURFACE HEIGHT IN 2-STEP SCHEME OF REAGENT DISK ROTATION LEGEND:
H····INITIALIZING POSITION (WITHOUT ROTATION)
RX(X=1~12)····DISTANCE FROM INITIALIZING POSITION (CCW)
LY(Y=1~12)····DISTANCE FROM INITIALIZING POSITION (CW)

AUTOMATED ANALYZER

TECHNICAL FIELD

The present invention relates generally to liquid-level detection devices that detect a liquid level of a liquid sample in an automated analyzer. More particularly, the invention concerns a liquid-level detection device constructed to detect a liquid level from a variation in capacitance due to contact of a reagent probe with the surface of the liquid.

BACKGROUND ART

In the liquid-level detection devices applied to automatic clinical analyzers, it has become common that a configuration having a liquid-level detection function added to a dispensing probe is employed to respond to a call for further improvement of measured-data accuracy. A recently known type of probe provided with a liquid-level detection function utilizes capacitance to use the probe itself as an electrode for liquid level detection.

The capacitive type detects the liquid level of a liquid sample by measuring a very insignificant variation in capacitance between the dispensing probe and the sample accommodated in a container, and utilizing the characteristic that contact of the probe with the surface of the liquid sample increases the variation in capacitance.

In the capacitive type, it is necessary that the variation in capacitance of the liquid sample be converted into an electrical signal variation. The bridge circuit schemes disclosed in JP-A-62-218818 and JP-A-63-259420 are known as recent examples of methods of the conversion. These conventional bridge circuit schemes including a bridge circuit to form, as part of the device components, an element having very small capacitance between a dispensing probe and a liquid sample, convert a variation in the capacitance into an output signal variation of the bridge circuit.

The differential circuit scheme disclosed in JP-A-02-59619 is known as a further example. In this conventional circuit scheme, a differential circuit is provided that differentiates a reference signal in accordance with the very small capacitance developed between a dispensing probe and a liquid sample, and a variation in the capacitance is converted into an output signal variation of the differential circuit.

In the capacitive schemes discussed above, the very small capacitance between the dispensing probe and the liquid sample needs to be measured accurately. In addition, reagent containers are mounted on a reagent disk. In the discussed schemes, however, oscillation of the liquid surface due to reagent disk rotation during liquid level detection has occasionally caused errors in detection results.

The reagent container disclosed in JP-A-2000-275251 is known as an example of a container constructed so as to suppress the oscillation of the liquid surface of a reagent as discussed above. This conventional reagent container is used in an automated analyzer that employs, for example, a rotary table or any other suitable transport means to transport the reagent container to a predetermined position at which the reagent that is the internal contents of the container is to be dispensed by probes or suction nozzles. The reagent container is constructed so as to suppress the oscillation of the liquid surface due to centrifugal force upon the container-accommodated reagent during the transport of the container, by generating fluid resistance in a centrifugal direction over a vertical range including a height region corresponding to an accommodation zone of the liquid, between a centrifugal proximal section of the smallest centrifugal force and a centrifugal distal section of the largest centrifugal force.

Japanese Patent Publication No. 3845305 proposes a reagent container as another example of a container constructed so as to suppress the oscillation of the liquid surface of a reagent, this reagent container being responsive to the oscillation occurring when the container is moved linearly by a belt conveyor or other means.

PRIOR ART LITERATURE

Patent Documents

Patent Document 1: JP-A-62-218818
Patent Document 2: JP-A-63-259420
Patent Document 3: JP-A-02-59619
Patent Document 4: JP-A-2000-275251
Patent Document 5: Japanese Patent No. 3845305

SUMMARY OF THE INVENTION

Problems to be Solved by the Invention

In the capacitive type, it is necessary that the very small capacitance between the dispensing probe and the liquid sample be measured accurately. In the meantime, processing by automated analyzers has been speeded up and the number of samples processed in individual clinical laboratory in hospitals or commercial labs, has increased. These tendencies, in turn, have increased the volume of reagents required for the day. Accordingly, reagent containers of larger capacities are also necessary. In addition, more rapid processing by such an automated analyzer has come to require faster rotation of a reagent disk on which to mount reagent containers. Greater centrifugal force, therefore, works upon the reagent containers. Consequently, the increase in centrifugal force augments the oscillation of the liquid surface of a reagent due to the increase in the capacity of the reagent containers, and the augmentation of the oscillation presents problems such as deterioration in reagent-dispensing accuracy, fouling of the reagent-dispensing probe, and an increase in dead volume of reagents.

A desirable method for improving reagent-dispensing accuracy while minimizing the deterioration thereof that is one of those problems is by measuring a liquid level accurately without oscillation of the reagent too significantly, even when a reagent container of a large capacity is used. An object of the present invention is to provide an automated analyzer based on the above considerations, the analyzer being capable of measuring a liquid level accurately, even when a large-capacity reagent container is used.

Means for Solving the Problems

In order to achieve the above object, the automated analyzer described herein comprises a control method in which, if a predetermined constant cycle time is defined as one unit, at least two units are used to transport a reagent disk with reagent containers mounted thereon, to a liquid-level detection position when a liquid level of a reagent is measured. The automated analyzer described herein comprises a control method in which, of all operational characteristics of a reagent disk, a moving distance thereof in a first cycle is longer than in a second cycle onward. In the control method of herein, reagent disk operation is of two units, in the control method of herein, a moving distance in the last cycle of reagent disk operation is equivalent to one reagent container of length, in the control method herein, the last cycle of reagent disk operation is started after the elapse of 1.5 seconds from an end of an immediately previous cycle, and in the control method herein, angular velocity in the last cycle of reagent disk operation is equal to or less than 0.3 rad/s.

The control means of the present invention is effective for an automated analyzer that measures a reagent quantity prior to analysis, and during the analysis, determines an insertion depth of a reagent-dispensing probe below a liquid level, from the pre-measured quantity of the reagent and a suction quantity thereof. In the automated analyzers comprising the present invention, although measuring the quantity of reagent requires one more cycle than measuring the quantity of reagent in one cycle of reagent disk operation (conventional method), errors in liquid-level measurement results due to the oscillation of the liquid surface of the reagent are suppressed to a minimum level. The present invention is characterized in that reagent disk control prior to analysis is distinguished from that conducted during the analysis. In addition, the present invention relates specifically to the reagent disk control conducted prior to the analysis and does not concern the reagent disk control conducted during the analysis. Throughput per unit time during the analysis, therefore, does not differ between a pre-application state of the present invention and a post-application state thereof.

Effects of the Invention

In an automated analyzer intended for qualitative/quantitative analysis of blood, urine, and other biological samples, and including a reagent disk for mounting a plurality of reagent containers thereon, any errors in liquid level measurement due to oscillation of a reagent liquid surface during rotation of the reagent disk are minimized, even when reagent containers of a large capacity are mounted.

BRIEF DESCRIPTION OF THE DRAWINGS

FIG. 11(a) is a diagram showing an example of reagent disk operation and FIG. 11(b) shows liquid-level measurement timing;

FIG. 13(a) shows liquid-surface height in a one-step scheme of reagent disk rotation. FIG. 13(b) shows liquid-surface height in a two-step scheme of reagent disk rotation.

MODE FOR CARRYING OUT THE INVENTION

Figure 1:
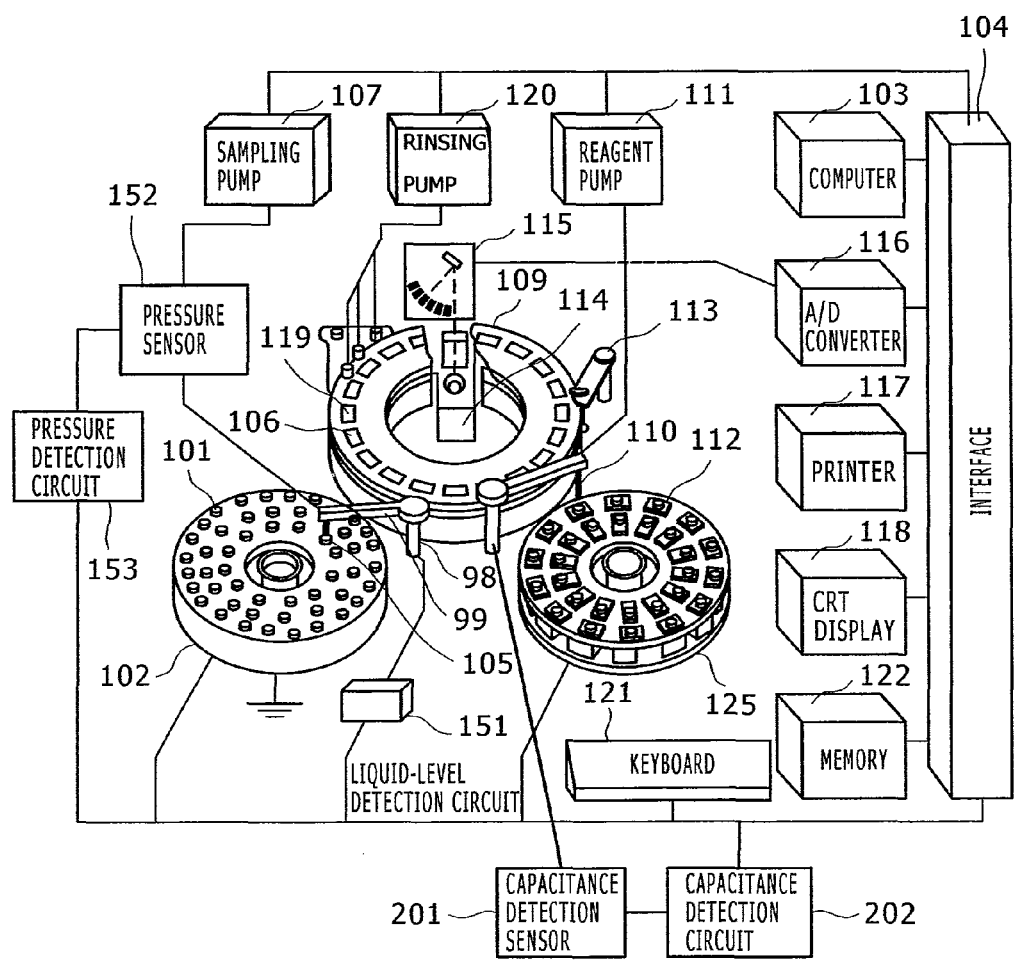
FIG. 1 is a schematic diagram showing an overall configuration of an automated analyzer to which the present invention is applied.

Hereunder, embodiments of the present invention are described sequentially from FIG. 1. FIG. 1 is a schematic diagram of an automated analyzer applying the invention, the diagram showing a dispensing mechanism and a peripheral region thereof. Constituent elements are common to those of a conventional analyzer in terms of configuration and function, so description of details is omitted. A sampling dispenser 98 has a sampling dispenser arm 99 that rotates in addition to moving vertically. A probe 105 disposed on the sampling dispenser arm 99 is adapted for suctioning a sample within a sample container 101 placed on a sample disk 102 formed to rotate clockwise and counterclockwise, and then discharging the sample into a reaction container 106. At a distal end of the probe 105, a nozzle that executes the suctioning and then discharging of the sample is provided so as to extend linearly in a vertical direction.

Referring to layout of sample containers 101 on the sample disk 102, as can be seen from FIG. 1, the sample containers are usually arranged directly on the disk 102 or constructed to be adaptable to universal layout that allows each sample container to be mounted on a test tube (not shown).

The configuration of the automated analyzer in FIG. 1 is described in further detail below. Bottles 112 that contain a reagent appropriate for a plurality of analytical items relating to a substance to be analyzed are arranged on a rotatable reagent disk 125. A probe of a reagent dispenser 110, mounted on a movable arm of the reagent dispenser, dispenses a predetermined amount of reagent from one of the reagent bottles 112 into a reaction container 106. At a distal end of the reagent dispenser probe, a nozzle that suctions and then discharges the reagent is provided so as to extend linearly in a vertical direction.

The probe 105 of the sample dispenser executes the suctioning and discharging of the sample, coupled with a sample-use syringe pump 107. The probe of the reagent dispenser 110 executes the suctioning and discharging of the reagent, coupled with a reagent-use syringe pump 111.

The items to be analyzed for each sample are entered from an input device such as a keyboard 121 or screen of a CRT display 118. Various units of the automated analyzer are controlled by a computer 103.

As the sample disk 102 rotates intermittently, the sample containers 101 are each moved to a sample-suctioning position and then after completion of the movement, the probe 105 of the sample dispenser is lowered into the sample container at rest. As the distal end of the probe 105 being lowered comes into contact with the liquid surface of the sample, a liquid-level detection circuit 151 outputs a detection signal and in accordance with this signal, the computer 103 controls the sampling dispenser arm 99 to stop the lowering operation of its driving unit.

After suctioning the predetermined amount of sample, the sampling dispenser probe 105 moves upward to an upper end position. While the sample dispenser probe 105 is suctioning the predetermined amount of sample, any suction in-channel pressure changes that may occur between the probe 105 and a flow channel of the sample syringe pump 107 are detected by a pressure sensor 152. Pressure signals detected at this time are monitored by a pressure detection circuit 153, and if an unusual pressure change is detected during the suctioning operation, it is most likely that the predetermined amount of sample is not being suctioned. For this reason, careful attention is drawn with an alarm about analytical results presented after the analysis.

After the predetermined amount of sample has been suctioned properly, the sampling dispenser arm 99 rotates in a horizontal direction, then the probe 105 moves downward at a position of a reaction container 106 on a reaction disk 109, and the probe 105 discharges the retained sample into the reaction container 106. The reaction container 106 containing the sample is next moved to a reagent-adding position, and upon completion of the movement, the probe of the reagent dispenser 110 dispenses the predetermined amount of reagent from one of the reagent bottles 112 corresponding to the desired analytical item, into the reaction container 106.

During the movement of the reaction container 106, a plurality of other reaction containers 106 cross a beam of light emitted from a light source 114, and absorbance or light-emission values of mixtures are measured by a photometer 115, a measuring instrument. A signal indicating the measured absorbance enters the computer 103 via an A/D converter 116 first and then an interface 104, and thus a concentration of the analytical item is calculated.

Analytical results are sent to the interface 104 and then printed out onto a printer 117 or output to the screen of the CRT display 118. Additionally, the analytical results are stored into a hard disk 122, a memory. Sound notification of an alarm can be combined with alarm display.

The reaction container 106 that has been subjected to the above optical measurements is rinsed at a position of a rinsing mechanism 119. A rinsing pump 120 supplies rinsing water to the reaction container 106. The rinsing pump 120 also discharges a reaction solution from the reaction container 106. In the example of FIG. 1, three arrays of container retainers are formed on the sample disk 102 so that three arrays of sample containers 101 can be set concentrically on the disk, and positions for sample-suctioning by the sampling dispenser probe 105 are provided, one in each array.

Details of the above reagent-dispensing operation are described below. After suctioning the predetermined amount of reagent from the appropriate reagent bottle 112, the probe of the reagent dispenser 110 discharges the reagent into a reaction container 106. At this time, a capacitance detection sensor 201 built into the probe of the reagent dispenser 110 measures capacitance between the probe and the container or a body accommodating the container. The capacitance detection sensor 201 is formed by a first electrode and second electrode or the like, which will be later described citing FIG. 2.

A signal that the capacitance detection sensor 201 has measured is monitored by a capacitance detection circuit 202. If the capacitance detection circuit 202 detects abnormal capacitance in the reagent being discharged, since it is most likely that the predetermined amount of reagent has not been suctioned, the circuit 202 adds an alarm to analytical results. The capacitance detection circuit 202 is formed by a capacitance-measuring unit 6 and a no-load suction detector 13, which will also be later described citing FIG. 2.

The capacitance detection circuit 202 is included in an abnormality detector that detects existence of any bubbles or air entrained in the liquid during dispensing. The capacitance detection circuit 202, as with other units, is controlled by the computer 103. During the monitoring of the dispensing operation in the above embodiment, the sampling dispenser probe measures a variation in the internal pressure of the flow channel during sample suctioning, and the reagent dispenser probe measures the capacitance occurring between the probe and reagent container during reagent discharging. In an alternative monitoring method, the sampling dispenser probe may measure the capacitance between the probe and the sample container during sample discharging, with the reagent dispenser probe measuring a variation in the internal pressure of the flow channel during reagent suctioning.

In addition, the measurements during monitoring may be conducted in suctioning or discharging operational timing of the dispenser probe. Furthermore, any information obtained during either or both of dispenser probe suctioning and discharging may be used for abnormality detection. Moreover, electrical conductivity and inductance may be used as dispensing-related physical quantities electrically measured.

In that case, the capacitance detection sensor and capacitance detection circuit in FIG. 1 are replaced by a signal detection sensor and a signal detection circuit, respectively. For example, a velocity detection sensor and a velocity detection circuit are provided to utilize measurement results on velocity. Additionally, if the liquid to be monitored contains magnetic particles, measurement results on magnetic field intensity of the particles may be used for abnormality detection of the dispensing operation. The capacitance detection sensor and capacitance detection circuit in FIG. 1 are replaced by a magnetism detection sensor and a magnetism detection circuit, respectively, in that case.

A liquid level of the sample in the sample container 101, and that of the reagent in the reagent bottle 112 are both detected during the dispensing of the liquids. The mixture inside the reaction container 106 containing the added sample and reagent is stirred by a stirrer 113.

Next, liquid quantity management of the reagent is described in detail below. The automated analyzer calculates a quantity of the liquid in one of the appropriate reagent bottles 112 placed on the reagent disk 125 prior to analysis. This process is called reagent registration since the liquid quantity is calculated from pre-registered information. During reagent registration, the automated analyzer reads a reagent ID (not shown) that is preassigned to the reagent bottle 112, or calculates the liquid quantity in accordance with user-registered information. During the reagent registration process, the automated analyzer transports the reagent bottle 112 on the reagent disk 125 to a dispensing location. After the reagent bottle 112 has been transported to the dispensing location, the capacitance detection sensor 201 within the probe of the reagent dispenser 110 measures the capacitance developed between the probe and the container or the container accommodation body. Based on results of the liquid quantity calculation, liquid quantity management of the reagent by the automated analyzer is conducted after a start of the analysis. During the analysis, the automated analyzer transports the reagent bottle 112 on the reagent disk 125 to the dispensing location in substantially the same manner as during reagent registration.

Figure 2:
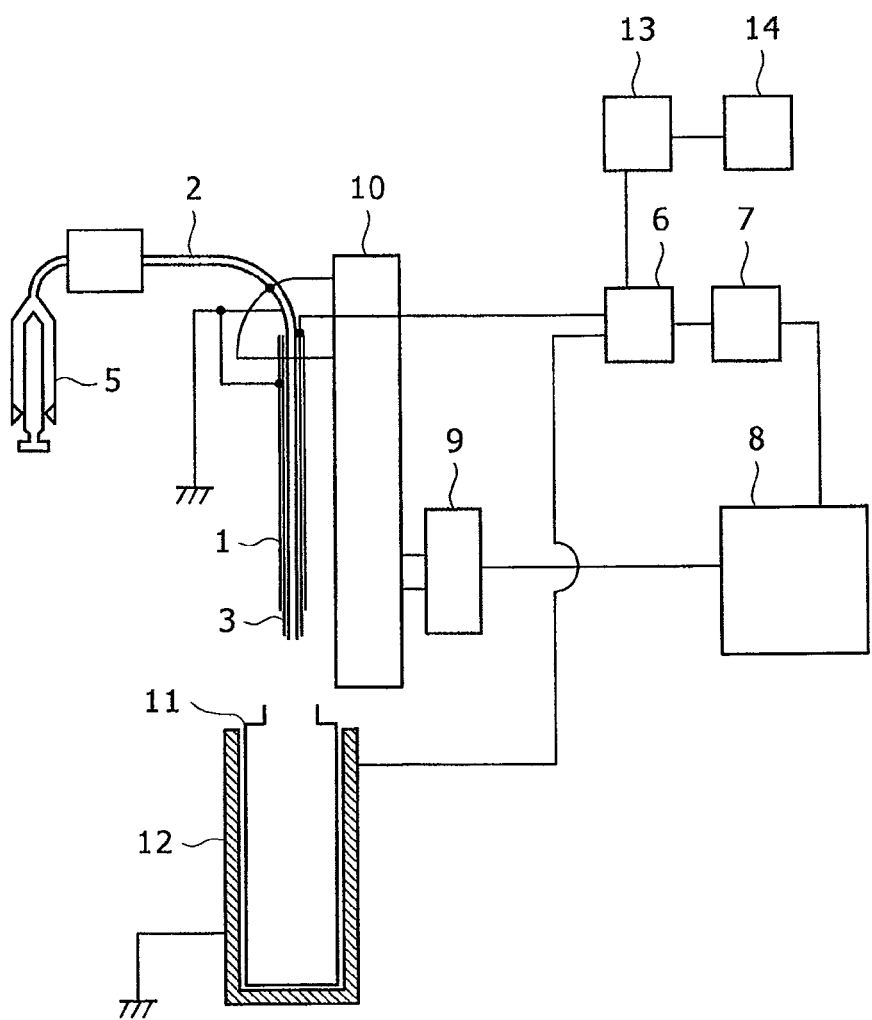
FIG. 2 is a schematic diagram relating to an embodiment of the present invention, the diagram showing a configuration of a liquid dispenser.

FIG. 2 shows one embodiment of a liquid dispenser according to the present invention. A nozzle is of a coaxial double-tube structure with a mobile-medium tube 2 that is an inner nozzle section, and with an electrical shield 1 that covers the tube 2. The shield 1 and tube 2 that are structural components of the nozzle are both formed from an electroconductive material such as stainless steel, and only the shield 1 is electrically grounded.

A distal end of the nozzle (i.e., a distal end of the tube 2) suctions and discharges the sample, the reagent, or the reaction solution between the sample and the reagent. Hereinafter, the sample, the reagent, or the reaction solution is referred to simply as the liquid. Since the nozzle is covered with the electroconductive shield 1, the nozzle end (distal end of the tube 2) that is one detection electrode is minimized in exposed-surface area, whereby any impacts upon the measurement of the capacitance between the nozzle and a section other than the second container accommodation body 12 as another detection electrode, are also minimized. The shield 1 also serves as a magnetic shield, which prevents liquid-level detector malfunctioning due to some kind of external noise arising from a motor 9 or the like.

A control unit 8 and the motor 9 work together to control a nozzle lift 10, thereby enabling vertical movement of the nozzle. A container 11 into which the liquid will be suctioned is encased in the container accommodation body 12. The container accommodation body 12 is formed from an electroconductive material such as aluminum, and electrically grounded. The tube 2 and the container accommodation body 12 are connected as the two capacitive electrodes to the capacitance-measuring unit 6. The liquid level can be detected by measuring the capacitance between the electrodes. The tube 2 on the nozzle operates as a first electrode. The container accommodation body 12 operates as a second electrode.

The capacitance-measuring unit 6 as an element for electrically measuring physical quantities, measures and detects the capacitance between the electrodes. The second electrode is replaceable by a further container (not shown) that will receive the liquid discharged from the container accommodation body 12. In that case, the further container is formed from an electroconductive material such as stainless steel or aluminum, and electrically grounded. A liquid level detection unit 7 is connected between the capacitance-measuring unit 6 and the control unit 8. The liquid level detection unit 7 determines whether the nozzle end is in contact with the liquid surface in the container.

Next, operation of the liquid dispenser is described below. The nozzle moves downward by means of the nozzle lift 10 in order to suction the liquid contained in the container 11. The capacitance-measuring unit 6 measures the capacitance between the tube 2 and container accommodation body 12 that are detection electrodes, and then transmits an output signal to the liquid level detection unit 7. The capacitance between the two detection electrodes is measured by the capacitance-measuring unit 6.

Upon the nozzle end coming into contact with the liquid surface by downward movement of the nozzle lift 10, the liquid level detection unit 7 sends a liquid level detection signal to the control unit 8. Upon receiving the liquid level detection signal, the control unit 8 stops the motor 9, thus stopping the downward movement of the nozzle. The two electrodes also function as a liquid level detector to detect the liquid level.

The predetermined amount of liquid in the container 11 is suctioned into the tube 2 by operation of the syringe 5 with the nozzle end in contact with the liquid surface. After this, the nozzle is lifted by upward movement of the nozzle lift 10 and then moved in a horizontal direction by a horizontal nozzle actuator not shown. Additionally, the nozzle is moved downward to a position above a further container (not shown) by the nozzle lift 10.

After the nozzle has been moved downward to a position above the further container (not shown) by the nozzle lift 10, the liquid that was suctioned into the tube 2 is discharged into the particular container (not shown) by the operation of the syringe 5. The tube 2 is filled with a mobile medium such as water or any other liquid, and the liquid that moves according to the particular operation of the syringe 5 is the medium that is suctioned and discharged.

When the nozzle suctions the liquid into the tube 2, the control unit 8 controls the vertical movement of the nozzle and the operation of the syringe so as to prevent the surface of the suctioned liquid from coming into contact with the tube 2 and the mobile medium contained therein. When the liquid that was suctioned into the tube 2 is discharged into the further container (not shown), the capacitance-measuring unit 6 measures the capacitance between the tube 2 and the container (not shown), and then the no-load suction detector 13 determines from a change in the capacitance whether the dispensing operation is abnormal. If the dispensing operation is abnormal, the no-load suction detector 13 sends an appropriate signal to an alarm generator 14, which then generates an alarm.

Following such alarm notification, a countermeasure such as issuing a request for re-analysis can be undertaken for the analysis that has encountered the dispensing abnormality. The no-load suction detector 13 is included in an abnormality detector that detects existence of any bubbles or air entrained in the liquid during dispensing.

Figure 3:
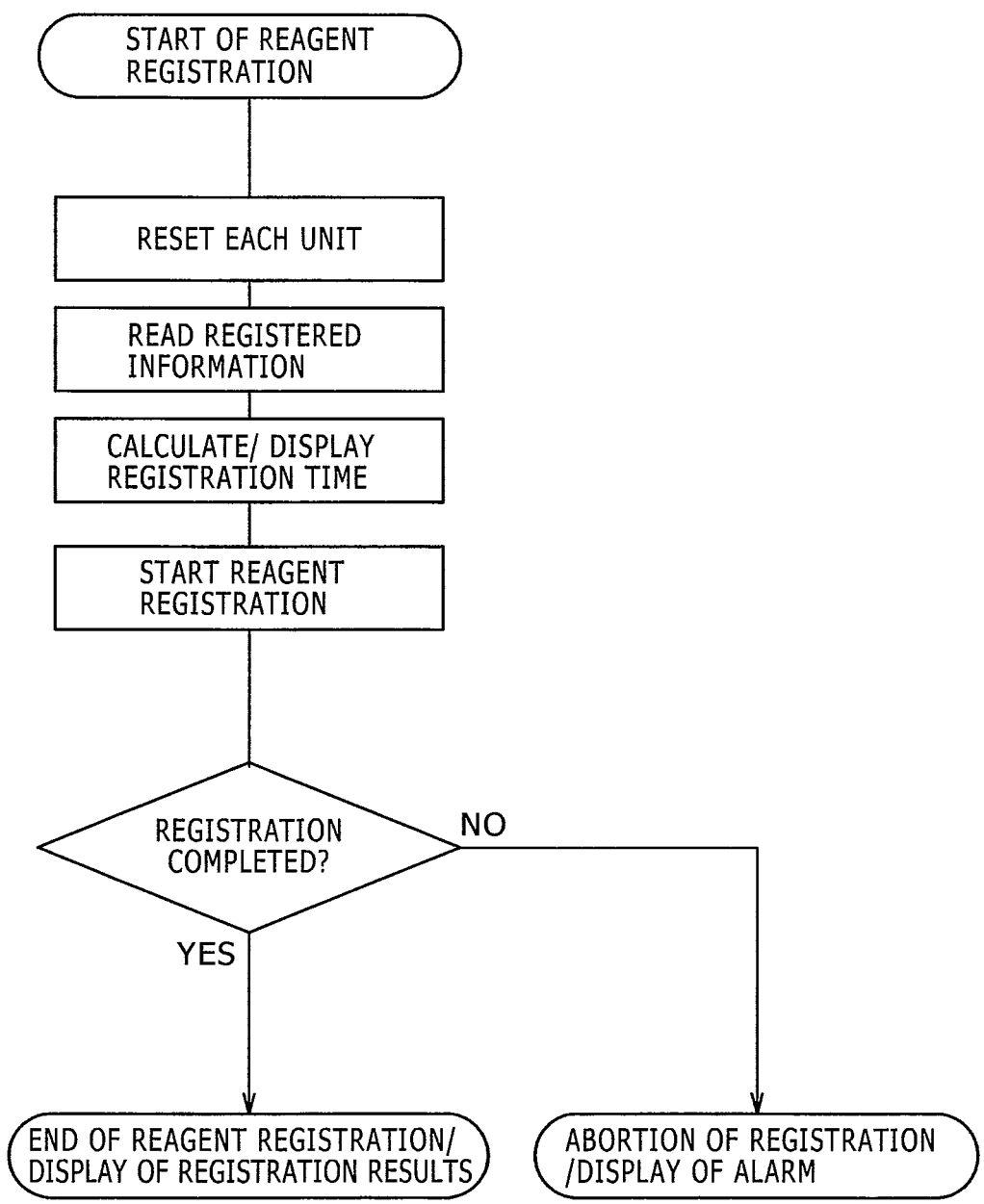
FIG. 3 is a diagram that relates to another embodiment of the present invention, the diagram showing a first flow of reagent registration.

Next, an operational flow of the reagent registration in the automated analyzer applying the present invention is described below with reference to FIG. 3. Upon starting the reagent registration, the automated analyzer resets the reagent disk, the dispensing probe, and other elements such as a reaction cell. For example, the resetting operation is accomplished by moving the reagent disk to an initializing position thereof during operational confirmation of each unit. At this time, the movement of the reagent disk to the initializing position uses a position identification element.

After the resetting operation, the automated analyzer measures a quantity of the liquid contained in a reagent container mounted on the reagent disk. During the reagent registration, an information reader (e.g., a bar code reader) reads an information transmission element (e.g., two-dimensional bar code) preaffixed to the reagent container, and identifies a location thereof and a reagent item, lot, and expiry date of the reagent. The information transmission element may be an RFID (radio-frequency identification). During the identification process, an alarm is displayed for expired reagent, thereby to notify to an operator that a time has come to replace the reagent container.

A time required for the reagent registration is next calculated from the number of reagent containers, and results are displayed on a screen of a personal computer (PC). Finally, if the reagent registration is completed as scheduled, registration results are displayed on the screen. If the reagent registration is aborted, registration results are not displayed and only an alarm displayed on the screen.

Figure 4:
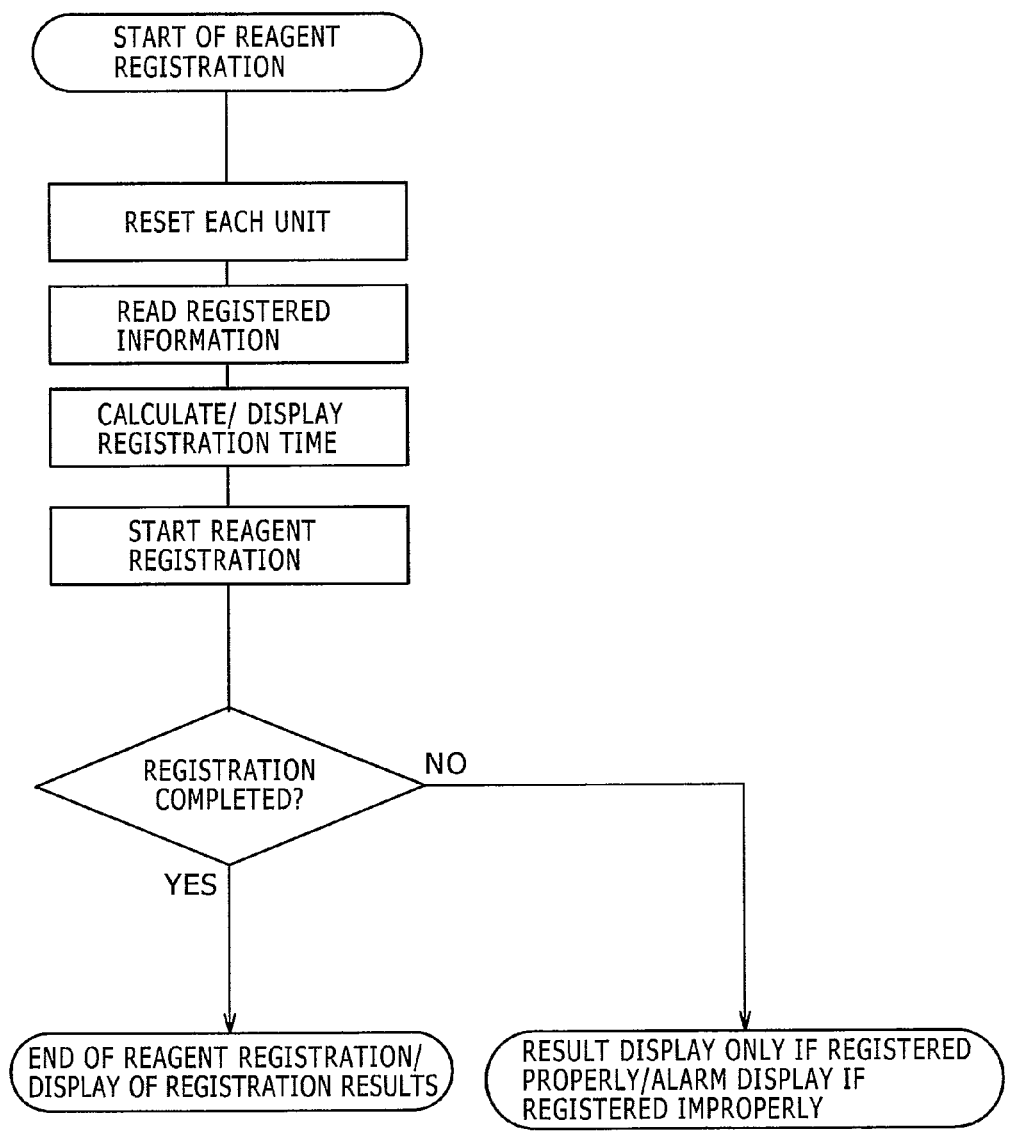
FIG. 4 is a diagram that relates to yet another embodiment of the present invention, the diagram showing a second flow of reagent registration.

If the reagent registration is aborted but registration results are obtained, the results may be screen-displayed for the reagent. A flow diagram applied in this case is shown in FIG. 4. If the reagent registration is aborted, only registration results may be displayed. In addition, if the reagent is not registered or an abnormality is detected during the quantitative measurement of the reagent, an alarm indicating that the registration has been aborted may be displayed on the screen without results being displayed for the reagent.

Next, operation of the reagent disk during the reagent registration is described below. In the flow diagrams of FIGS. 3 and 4, if the first reagent container is present at the dispensing location, the liquid surface of the reagent is measured without immediately preceding rotation of the reagent disk. If a plurality of reagent containers exist on the reagent disk, the second and subsequent reagent containers are each transported to the dispensing location using two steps of reagent disk operational control. For example, the two-step transport of a reagent container to the dispensing location is divided into a first step of transporting the reagent container to a container-mounting position immediately next to the dispensing location, and a second step of moving the container to the dispensing location.

Figure 6:
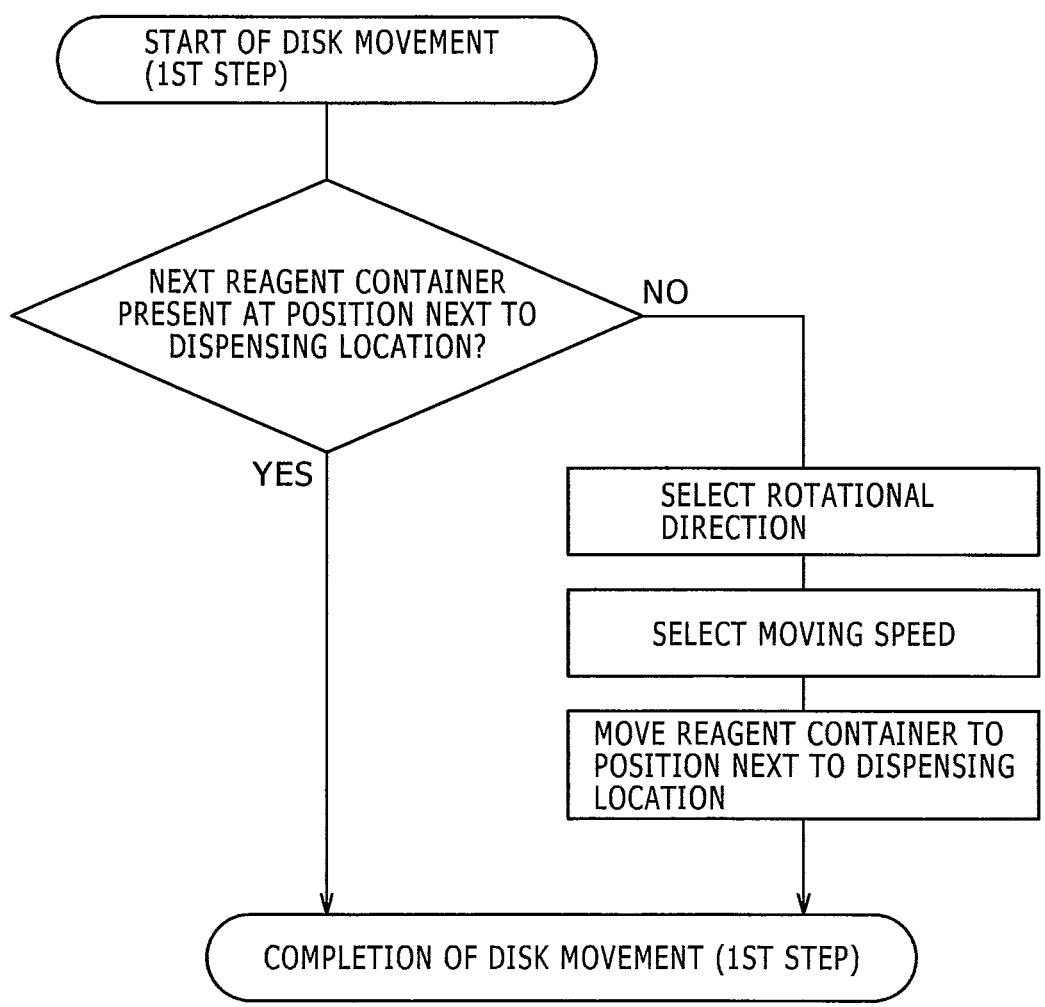
FIG. 6 is a diagram that relates to a further embodiment of the present invention, the diagram showing a process flow of disk movement (first step)

The operation of the reagent disk in the first step is described below in accordance with a flow diagram of FIG. 6. After the reagent registration of the first reagent container, the first step is omitted if the second reagent container is present at the location immediately next to the dispensing location. If the second reagent container is present at a location that is at least two container-mounting positions away from the dispensing location, a rotational direction of the reagent disk and a moving speed thereof are selected from a relationship in position between the reagent container and the dispensing location. After this, the reagent container is transported to the container-mounting position immediately next to the dispensing location.

Figure 5:
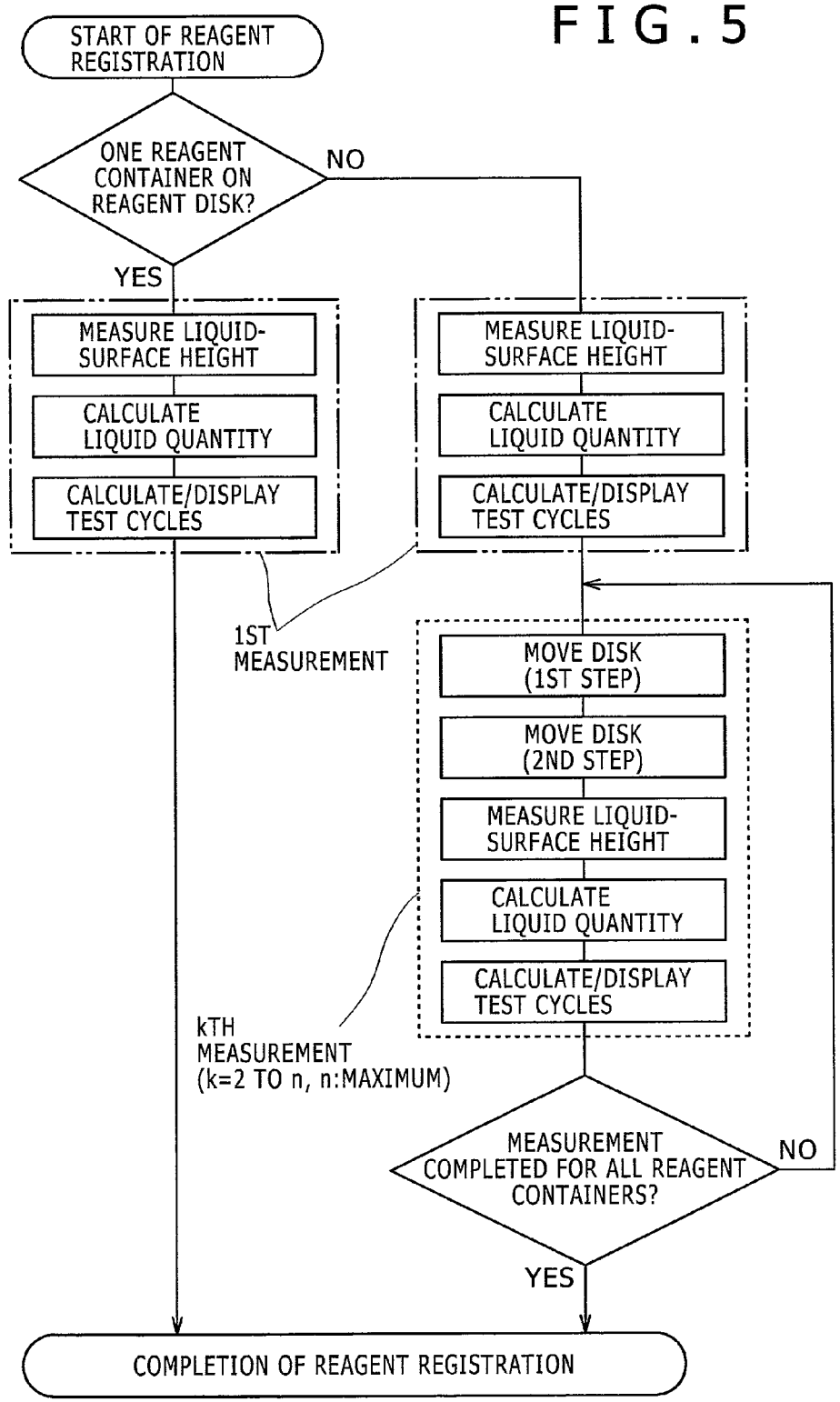
FIG. 5 is a diagram that relates to a further embodiment of the present invention, the diagram showing an operational starting flow of reagent registration.

In the second step, the reagent container at the position immediately preceding or following the dispensing location is transported to the dispensing location. After this, the liquid level of the reagent is measured, the liquid quantity is calculated, and effective test cycles are calculated. After the measurement of the liquid level in the second reagent container, the liquid levels in the third and subsequent reagent containers are measured in order. The process from the operational start of the reagent registration to completion thereof follows a flow diagram of FIG. 5.

Next, a liquid-level measuring sequence in a case of mounting a plurality of reagent containers on the reagent disk is described below. The liquid-level measuring sequence is based on, for example, ascending order of position numbers assigned on the reagent disk. The start of the reagent registration moves the reagent disk to the initializing position during the resetting operation. The initializing position is fixed, regardless of the position of the first reagent container to undergo the reagent registration, and if the first reagent container is absent at the dispensing location, this reagent container is transported to the dispensing location. During the reagent disk movement immediately preceding the liquid level measurement, the reagent container is desirably transported so that liquid-surface oscillation of the reagent is minimized.

For example, under conditions that one reagent container is mounted on the reagent disk, that the reagent container is present in its initializing position, and that the liquid is dispensed at this initializing position, the reagent disk will not rotate immediately before the liquid level is measured. During the liquid level measurement in this case, the oscillation of the reagent due to reagent disk rotation will not occur.

Under other conditions that one reagent container is registered and that the reagent container is absent at the dispensing location, after the resetting operation, the reagent container will be transported to the dispensing location immediately before the liquid level is measured. To implement the transport, several functions will be needed for minimizing the oscillation of the liquid due to reagent disk rotation. Firstly, the reagent disk will need to include a plurality of position identification elements (not shown).

Figure 7:
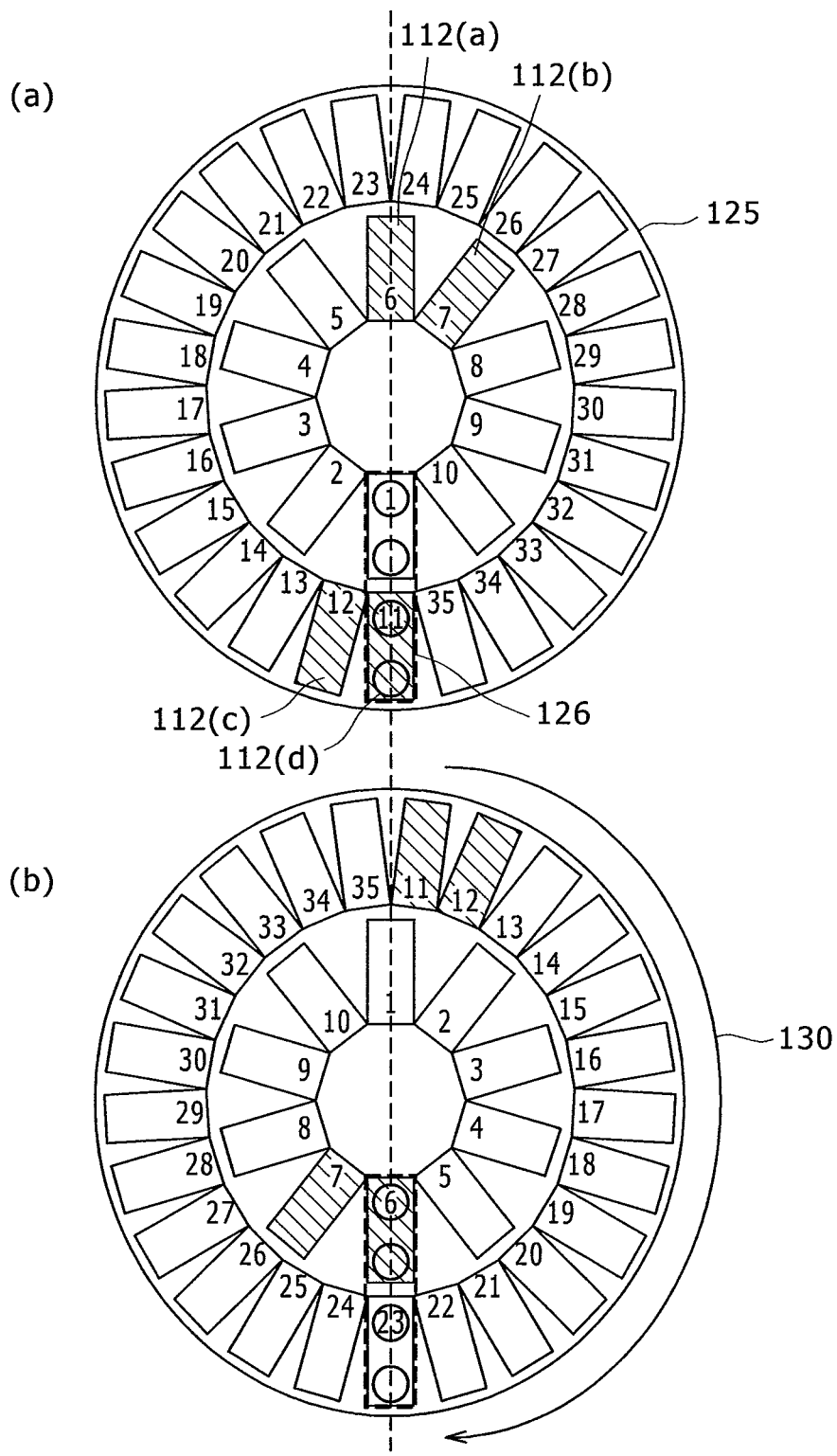
FIGS. 7(a) and 7(b) are diagrams that relate to a further embodiment of the present invention, the diagram showing an example of reagent disk operation in which the disk is controlled by one driving element.

Operation of the reagent disk existing when the disk is configured to be controlled by one driving element and reagent containers are placed on the disk as shown in FIG. 7(*a*) is described below. For the measurements in ascending order of the position numbers on the reagent disk, liquid levels are measured at positions 6, 7, 11, 12, in that order. As shown in FIG. 7(*b*), when reagent container No. 6 is moved to the dispensing location prior to the liquid-level measurement, the movement of this reagent container from the initializing position to the dispensing location uses a position identification element equipped on the reagent disk.

Figure 8:
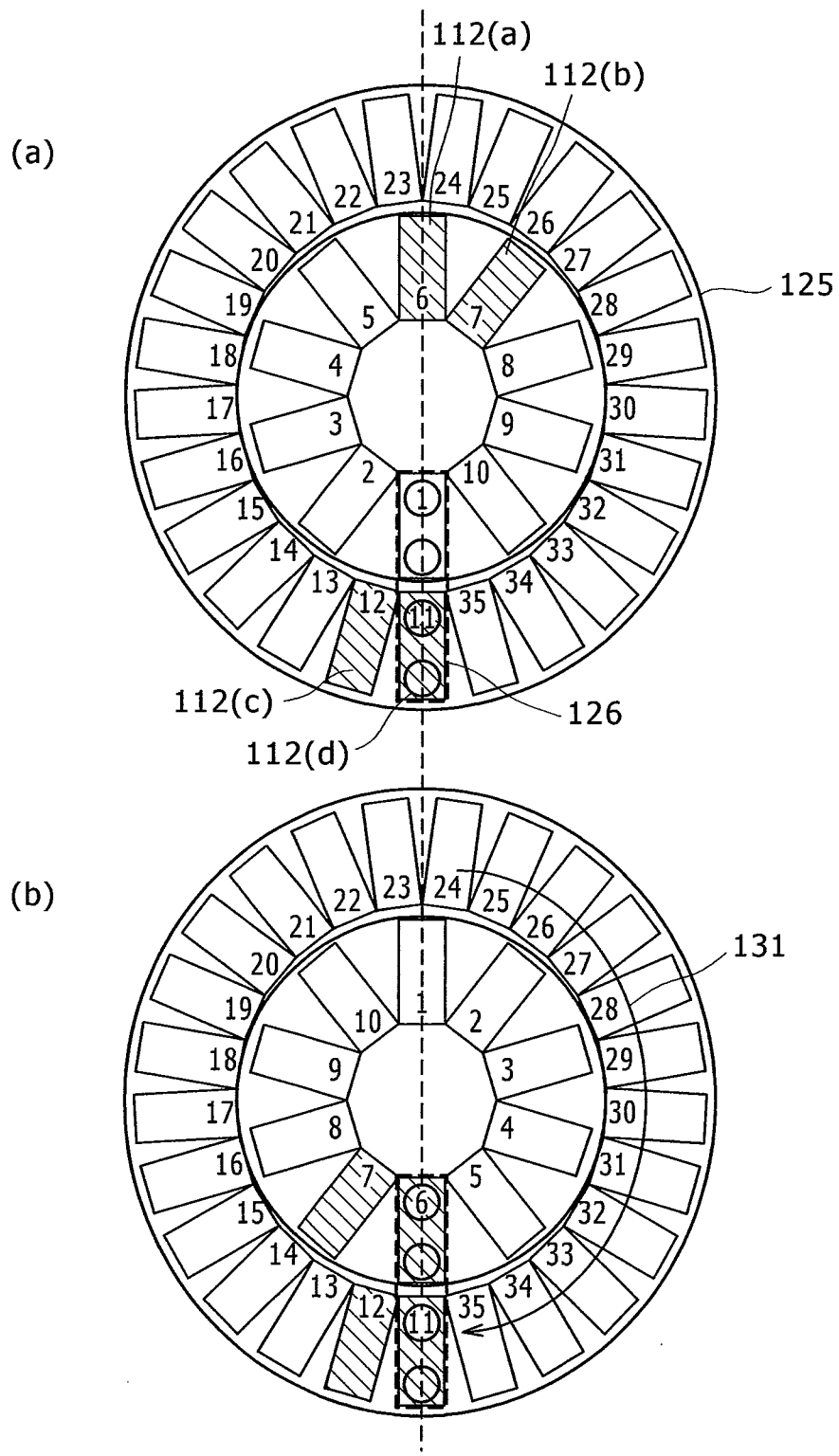
FIGS. 8(a) and (b) are diagrams that relate to a further embodiment of the present invention, the diagram showing an example of reagent disk operation in which the disk is controlled by two driving elements.

Under another possible configuration, an independent driving element is present on inner and outer surfaces each of the reagent disk (the inner and outer surfaces here refer to those existing when seen in plan view) and each of the driving elements conducts independent control of the disk. In this configuration, the inner and outer surfaces of the reagent disk each include a plurality of position identification elements (not shown). If reagent containers are placed on the disk as shown in FIG. 8(*a*), the liquid level measurements in ascending order of the position numbers on the reagent disk are conducted at positions 6, 7, 11, 12, in that order.

In this configuration, the inner and outer surfaces of the reagent disk operate independently and each reagent container on these surfaces is moved from the initializing position to the dispensing location. In an example of FIG. 8(*b*), before the liquid level is measured, reagent container No. 6 is moved to the dispensing location by rotating the inner surface of the reagent disk.

In a special case, where the first reagent container to be subjected to reagent registration following completion of the resetting operation is present at the dispensing location, there is no need to move the reagent disk immediately before the liquid level is measured. In this special case, therefore, the oscillation of the reagent due to reagent disk rotation is insignificant, compared with oscillation levels in other cases, and thus, liquid-level measurement accuracy correspondingly improves.

Figure 9:
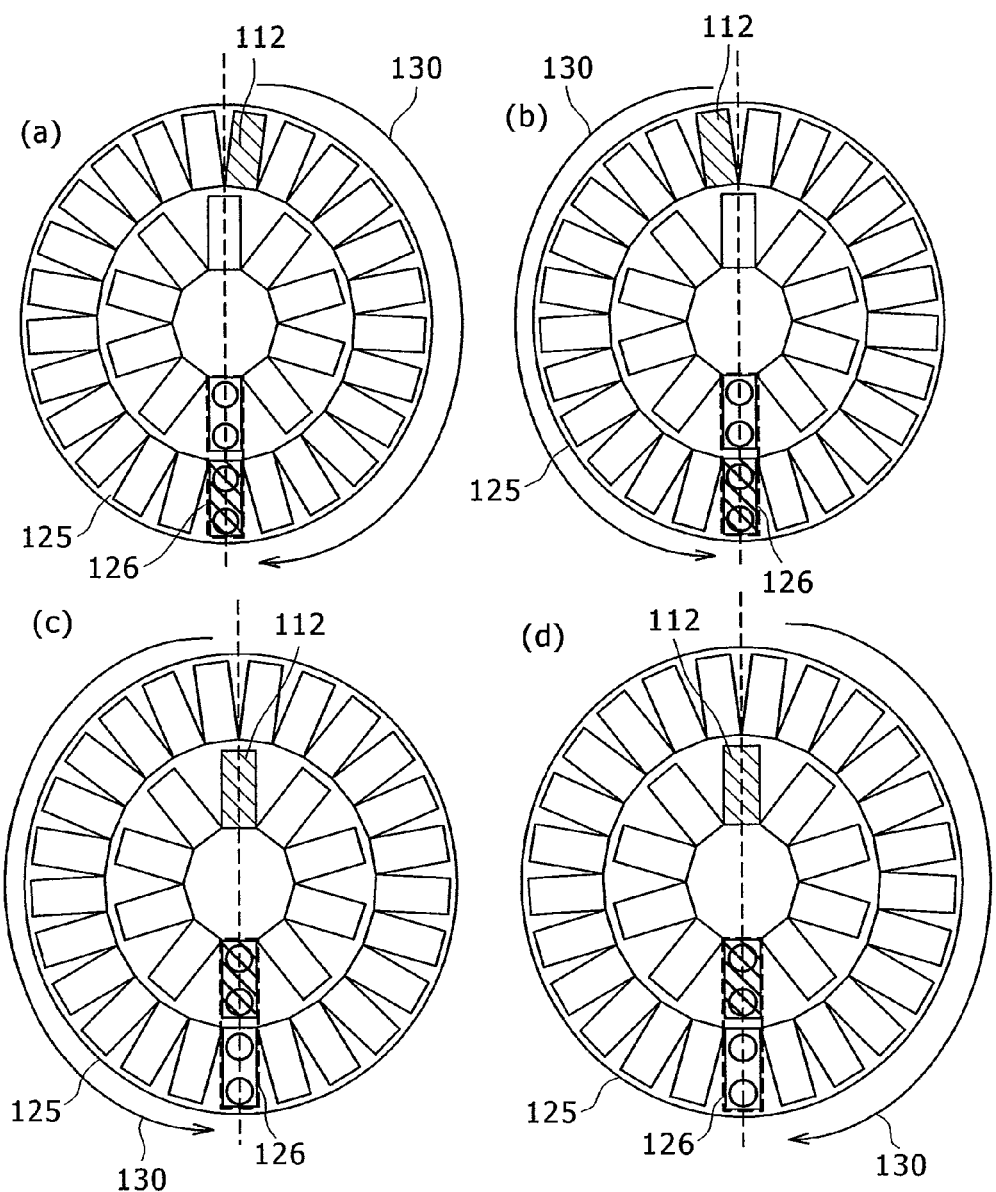
FIG. 9(a)-(d) are diagrams diagram showing an example of reagent disk operation in a conventional automated analyzer.

Next, a method of controlling the reagent disk during reagent registration is described below. FIG. 9 shows an example of reagent disk operation in the conventional automated analyzer. A rotational direction of the reagent disk and a moving speed thereof are selected from a relationship in position between a reagent container and a dispensing location, and then the reagent container is transported to the dispensing location before the liquid level is measured. As shown in FIGS. 9(*a*) and 9(*b*), the rotational direction of the reagent disk is selected so that a moving distance is minimized. Since moving distances in FIGS. 9(*c*) and 9(*d*) are the same, pre-registered rotational direction and moving speed are selected.

Figure 10:
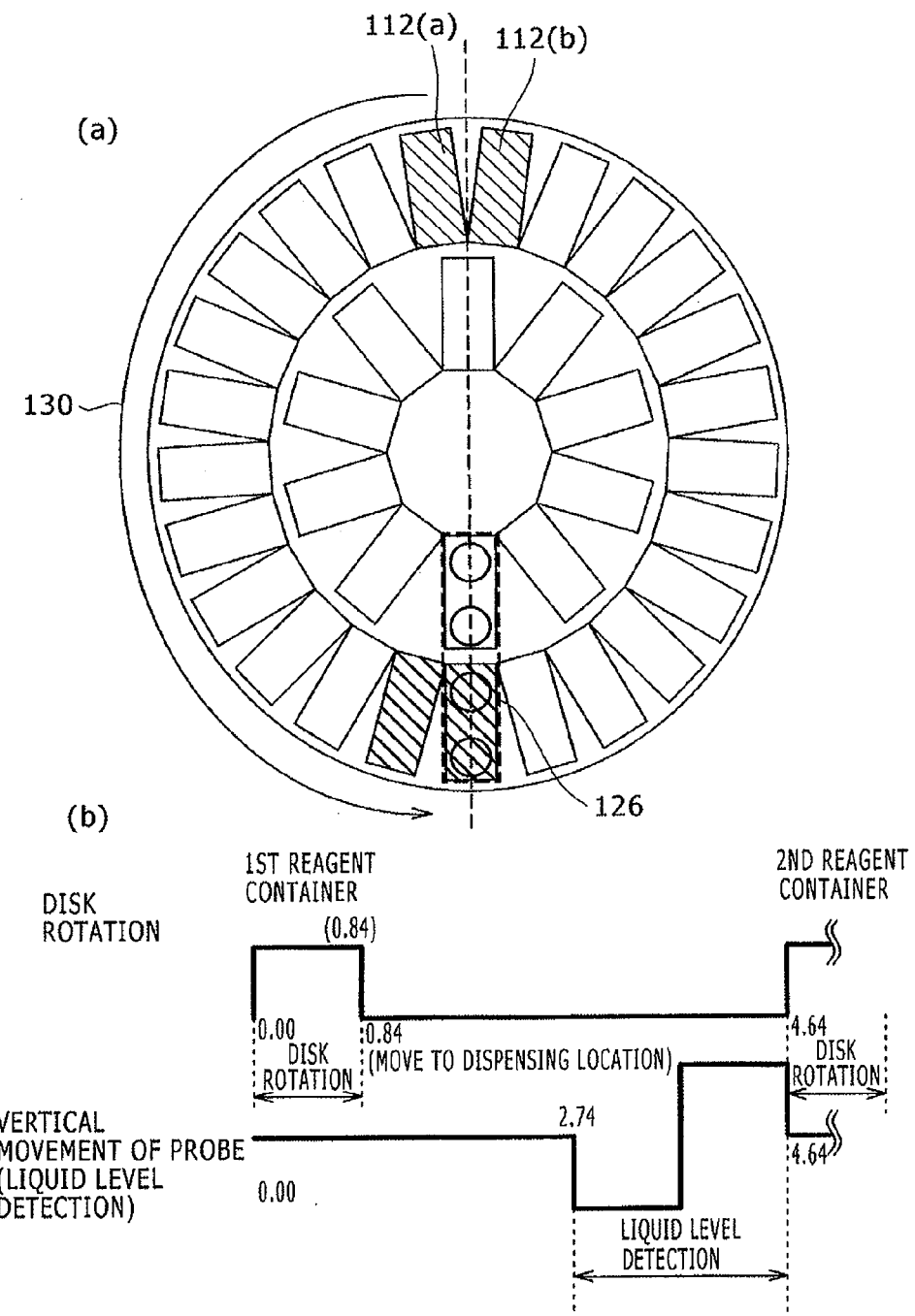
FIG. 10(a) is a diagram that shows reagent disk operation and FIG. 10(b) shows liquid-level measurement timing in the conventional automated analyzer.

Next, the reagent disk operation and liquid-level measurement timing in the conventional automated analyzer are described below. As shown in FIGS. 10(*a*) and 10(*b*), a dispenser probe operates after the reagent container has been transported to the dispensing location. If an operation time of the reagent disk is constant without being dictated by a position of the reagent container existing before reagent registration, when the container is present at a place distant from the dispensing location, the reagent disk needs to be transported as rapidly as possible.

As the moving speed becomes higher, centrifugal force due to the rotation of the reagent disk increases, which in turn augments the oscillation of the reagent, associated with the rotation of the reagent disk. The increase in the oscillation of the reagent increases nonuniformity of measurement results, so it is desirable that the method of operating the reagent disk be improved for minimum oscillation.

Figure 11:
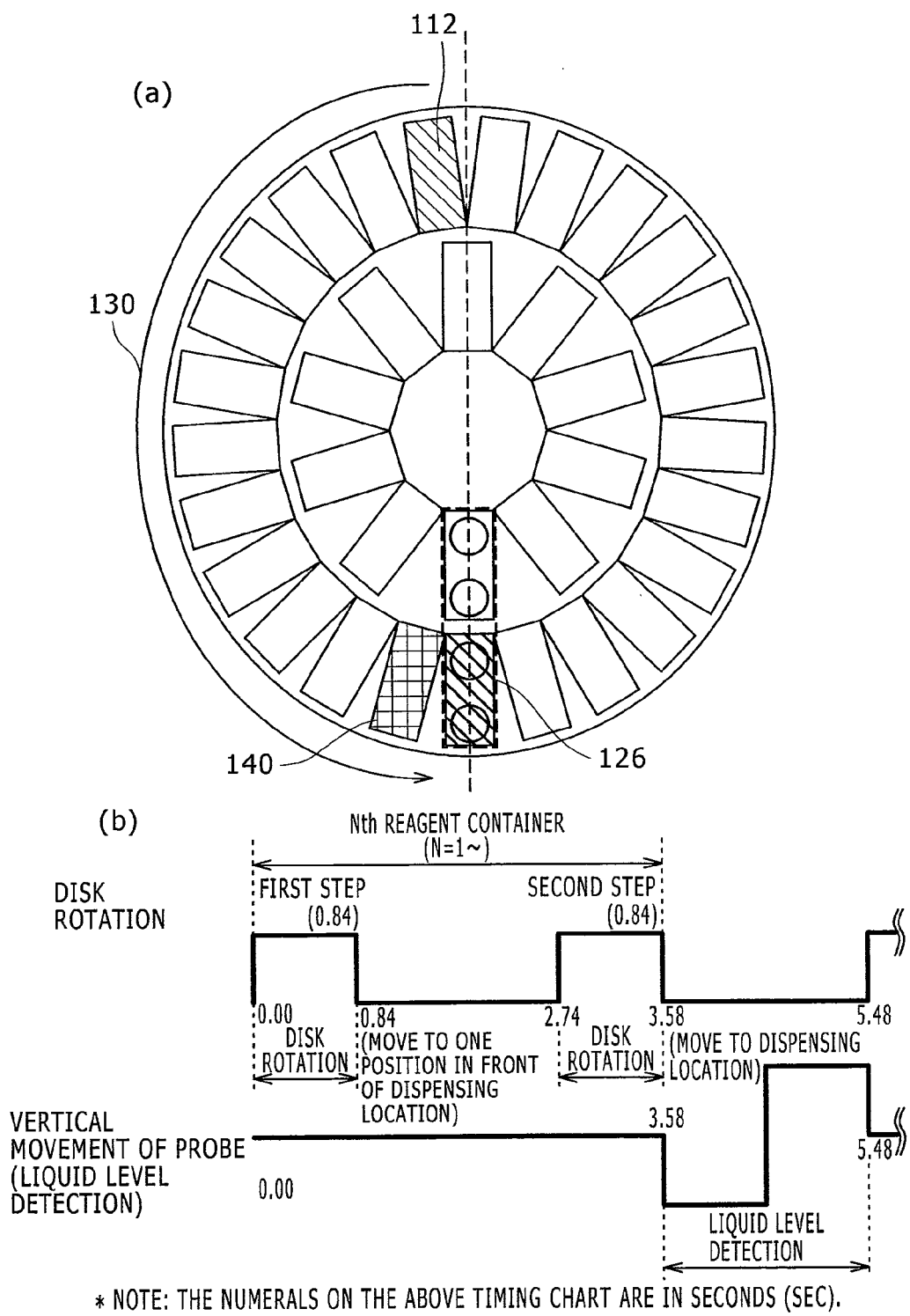
FIGS. 11(a) and 11(b) relate to a further embodiment of the present invention.

The present invention proposes, as a way to achieve the improvement, a method of dividing the operational control of the reagent disk into two steps. As shown in FIG. 11(a), in a first step, the reagent container is moved to a position in immediate front of the reagent-dispensing location, and then in a second step, the container is further moved to the reagent-dispensing location. Additionally, as shown in FIG. 11(b), a sufficient interval of time needs to be provided between execution of the first step and that of the second step to minimize any impacts of the oscillation due to reagent disk rotation when the liquid level is measured.

The interval between the first step and the second step is determined using liquid oscillation simulation results. Simulation was conducted under conditions that as shown in FIGS. 7 and 8, a total of 35 reagent containers, 10 on the inner surface of the reagent disk and 25 on the outer surface thereof, are arranged, that reagent containers are arranged on the outer surface of the reagent disk, and that an operating radius of the disk is 230 mm and an angular velocity thereof is 7.5 rad/s. In addition, the reagent containers were each divided into two segments, one with a cross-sectional area equivalent of 1,800 $mm^2$ and the other with a cross-sectional area equivalent of 600 $mm^2$, and among all reagent containers internally equipped with a partition plate to suppress the liquid oscillation associated with reagent disk rotation, only those with the 1,800 $mm^2$ cross-sectional area were adopted as a model. Simulation results on the oscillation of the liquid at the dispensing location are shown in FIG. 12.

Figure 12:
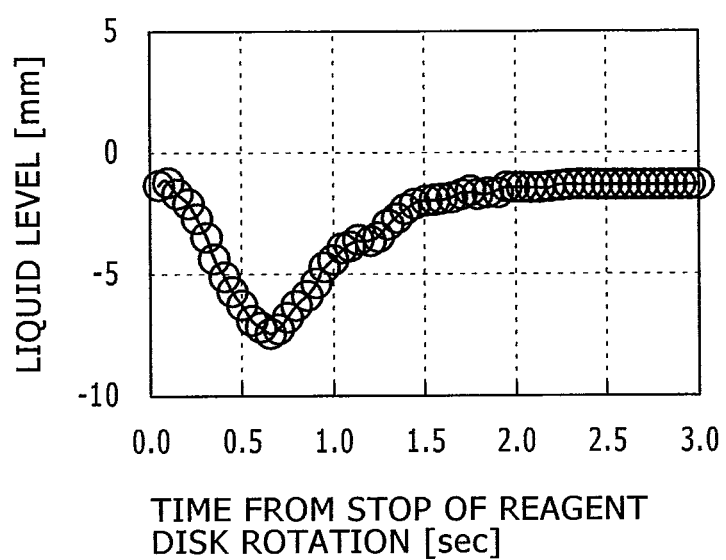
FIG. 12 is a diagram that relates to the reagent disk operation in the conventional automated analyzer, the diagram showing an example of liquid-level variations simulation results obtained after reagent disk rotation.

As shown in FIG. 12, variations in the internal liquid level of the reagent container become a maximum after 0.6 to 0.7 seconds, and decrease to 0 mm after 1.5 seconds, from a stop of reagent disk rotation. Under these conditions, setting data so that the second step is started after the elapse of at least 1.5 seconds from the disk operation in the first step makes suppressible the impacts of the oscillation due to reagent disk rotation.

Another way to reduce the impacts of the oscillation due to reagent disk rotation is by rotating the reagent disk at the angular velocity appropriate for the operating radius. For example, if, as shown in FIGS. 7 and 8, 10 reagent containers are arranged on the inner surface and 25 reagent containers are arranged on the outer surface, a moving distance (or rotational angle) for disk movement through one reagent container of space is 0.63 rad (=36°) on the inner surface or 0.25 rad (=14.4°) on the outer surface. Given a constant operational cycle time of the reagent disk, the angle velocity of the reagent disk increases as the moving distance increases.

Figure 13:
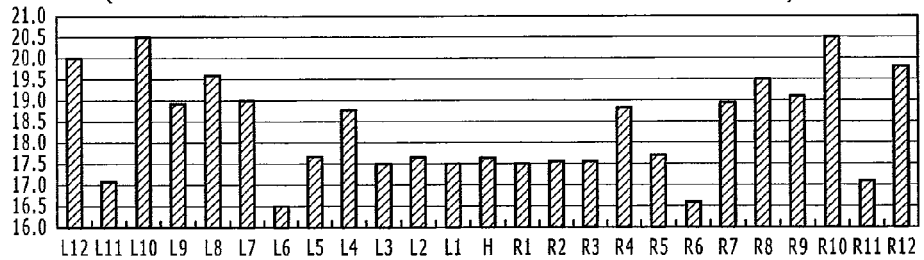
FIG. 13 is a diagram that relates to reagent disk operation, showing examples of liquid-level detection errors for comparison between the conventional method and the present invention.
Figure 13:
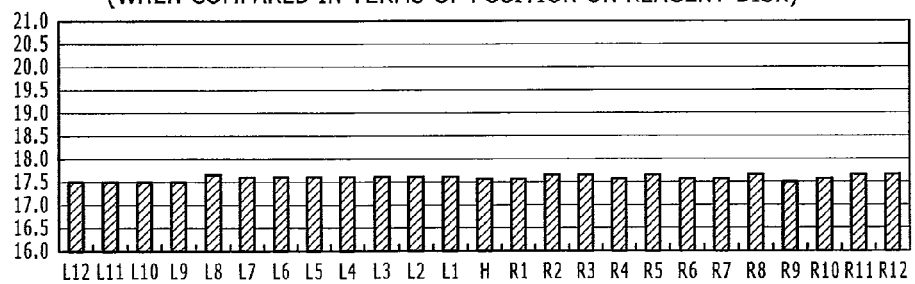

The impacts of the oscillation due to reagent disk rotation can be suppressed if the angular velocity of the reagent disk is selected appropriately according to the particular moving distance, characteristics (viscosity and contact angle) of the liquid reagent, and presence/absence of a surface-active agent in the reagent. FIG. 13, for example, shows liquid-surface height measurement results in an automated analyzer equipped with reagent containers arranged on an outer surface of a reagent disk having an operating radius of 230 mm, each of the reagent containers having been divided into a segment whose cross-sectional area equivalent is 1,800 $mm^2$ and a segment whose cross-sectional area equivalent is 600 $mm^2$.

As shown in FIG. 13, in comparison of liquid surface height between one-step reagent disk rotation scheme and the two-step reagent disk rotation scheme in the present invention, maximum variations in measured height are 0.1 mm at all adjacent container-mounting positions up to the third thereof from the initializing position, on both left and right sides. At locations that are distanced through at least four container-mounting positions of space from the initializing position, on the other hand, maximum variations are as great as 4.0 mm in the one-step scheme.

FIG. 13(b) shows measurement results that were obtained by setting two operation cycles for the reagent disk, setting the moving distance of the second cycle to be equivalent to one container-mounting position of distance, and assigning an angular velocity of 0.3 rad/s. In the two-step scheme, measurement results on the liquid surface heights at the initializing position and at other locations are insignificant in variation level, compared with those of the one-step scheme, and a maximum variation is 0.4 mm. FIG. 13 shows measurement results obtained when reagent containers were arranged on the outer surface of the reagent disk. If reagent containers are arranged on the inner surface of the reagent disk, however, the moving distance corresponding to the second cycle is equivalent to one container-mounting position of distance and the angular velocity is 0.7 rad/s. Under these conditions, the impacts of the oscillation due to reagent disk rotation are suppressed as effectively as in FIG. 13.

In the configuration of the present invention, the distance through which the reagent disk moves immediately before the liquid level is measured is one reagent container-mounting position of distance and the impacts of the oscillation due to reagent disk rotation are suppressed effectively, compared with the impacts in the conventional analyzer configuration. The automated analyzer according to the present invention, therefore, reduces variations in liquid-level measurement results and accurately measures liquid levels.

DESCRIPTION OF REFERENCE NUMERALS

1 Shield
2 Mobile medium tube
3 Detection electrode
5 Syringe
6 Capacitance-measuring unit
7 Liquid level detection unit
8 Control unit
9 Motor
10 Nozzle lift
11 Container
12 Container accommodation body
13 No-load suction detector
14 Alarm generator
98 Sampling mechanism (dispenser)
99 Sampling arm
101 Sample container
102 Sample disk
103 Computer
104 Interface
105 (Sampling dispenser) probe
106 Reaction container
107 Sample syringe pump
109 Reaction disk
110 Reagent dispenser
111 Reagent syringe pump
112 and 112(a), (b), (c), (d) Reagent bottles
113 Stirrer
114 Light source 115 Photometer
116 A/D converter
117 Printer
118 CRT display
119 Rinsing mechanism
120 Rinsing pump
121 Keyboard
122 Hard disk
125 Reagent disk
126 Reagent dispensing location
130 Reagent disk rotational direction
131 Reagent disk (inside) rotational direction
140 Position of reagent container (in front of dispensing location) after first cycle during two-cycle reagent disk rotation
151 Liquid-level detection circuit
152 Pressure sensor
153 Pressure detection circuit
201 Capacitance detection sensor
202 Capacitance detection circuit

The invention claimed is:

1. An automated analyzer comprising:
a plurality of reagent containers that accommodate a reagent;
a plurality of reaction containers that accommodate an analysis item to be analyzed, which includes the reagent and a sample, both the reagent and the sample are dispensed into the plurality of reaction containers;
a probe that pipettes the reagent from the reagent container;
information transmission means that transmits information about the reagent which is provided on the reagent container;
information reading means that reads the reagent information from the information transmission means;
a reagent container transport mechanism that mounts the plurality of the reagent containers, and transports the reagent and containers;
a control mechanism that operationally controls the reagent container transport mechanism in units of a predetermined constant cycle time; and
a photometer configured to measure an absorbance value of the analysis item in the plurality of reaction containers;
the automated analyzer further comprising:
a liquid-level detection mechanism provided in at least one of reagent container stopping positions on the reagent container transport mechanism, and configured to detect a liquid level of the reagent accommodated in the reagent container;
wherein, the control mechanism is configured to transport using at least two successive cycles, one of the plurality of reagent containers that is to be subjected to detection of the liquid level of the reagent to the at least one reagent container stopping positions at which the liquid-level detection mechanism is provided, and measure a liquid volume of the reagent in the reagent container by the liquid-level detection mechanism;
wherein, the control mechanism is configured to, determine an insertion depth of the probe below a liquid level on the basis of the measured liquid volume and a suction quantity of the reagent;
wherein, the control mechanism is configured to analyze the analysis item on the basis of the absorbance value measured by the photometer; and
wherein, the moving distance of the reagent container in the last cycle of the at least two successive cycles is equivalent to a rotational moving distance corresponding to one reagent container in the reagent container transport mechanism.

2. The automated analyzer according to claim 1, wherein a moving distance of the reagent container in the at least two successive cycles of time is such that a moving distance of the reagent container in the first of the cycles is longer than a moving distance of the reagent container in any of the cycles following the first cycle.

3. The automated analyzer according to claim 1, wherein the at least two successive cycles are two cycles of time.

4. The automated analyzer according to claim 1, wherein when the reagent container is moved in the at least two successive cycles, operation of the reagent container in the last of the cycles is started after at least 1.5 seconds from the cycle immediately preceding the last cycle.

5. An automated analyzer comprising:
a plurality of reagent containers that accommodate a reagent;
a plurality of reaction containers that accommodate an analysis item to be analyzed, which includes the reagent and a sample, both the reagent and the sample are dispensed into the plurality of reaction containers;
a probe that pipettes the reagent from the reagent container;
information transmission means that transmits information about the reagent which is provided on the reagent container;
information reading means that reads the reagent information from the information transmission means;
a reagent container transport mechanism that mounts the plurality of the reagent containers, and transports the reagent containers;
a control mechanism that operationally controls the reagent container transport mechanism in units of a predetermined constant cycle time; and
a photometer configured to measure an absorbance value of the analysis item in the plurality of reaction containers;
the automated analyzer further comprising:
a liquid-level detection mechanism provided in at least one of reagent container stopping positions on the reagent container transport mechanism, and configured to detect a liquid level of the reagent accommodated in the reagent container;
wherein, the control mechanism is configured to, transport, using at least two successive cycles, one of the plurality of reagent containers that is to be subjected to detection of the liquid level of the reagent to the at least one reagent container stopping positions at which the liquid-level detection mechanism is provided, and measure a liquid volume of the reagent in the reagent container by the liquid-level detection mechanism;
wherein, the control mechanism is configured to, determine an insertion depth of the probe below a liquid level on the basis of the measured liquid volume and a suction quantity of the reagent;
wherein, the control mechanism is configured to analyze the analysis item on the basis of the absorbance value measured by the photometer;
wherein, a moving distance of the reagent container in the at least two successive cycles of time is such that a moving distance of the reagent container in the first of the cycles is longer than a moving distance of the reagent container in any of the cycles following the first cycle; and wherein an angular velocity of the reagent container in the last cycle of the at least two successive cycles is equal to or less than 0.3 radians per second.

* * * * *